United States Patent [19]
Olson

[11] Patent Number: 5,803,084
[45] Date of Patent: Sep. 8, 1998

[54] THREE DIMENSIONAL VECTOR CARDIOGRAPHIC DISPLAY AND METHOD FOR DISPLAYING SAME

[76] Inventor: Charles Olson, 43 Lewis Ct., Huntington Station, N.Y. 11743

[21] Appl. No.: 760,986

[22] Filed: Dec. 5, 1996

[51] Int. Cl.[6] .................................................. A61B 5/0402
[52] U.S. Cl. .......................................... 128/699; 128/710
[58] Field of Search .................................... 128/696, 699, 128/710

[56] References Cited

U.S. PATENT DOCUMENTS

| | | |
|---|---|---|
| 3,186,403 | 6/1965 | Bassett . |
| 3,333,580 | 8/1967 | Fawcett .................................... 128/699 |
| 3,710,174 | 1/1973 | Cerniglia, Jr. . |
| 3,816,849 | 6/1974 | Kinoshita et al. . |
| 4,136,690 | 1/1979 | Anderson et al. ....................... 128/699 |
| 4,175,337 | 11/1979 | Benjo . |
| 4,292,977 | 10/1981 | Krause et al. . |
| 4,478,223 | 10/1984 | Allor . |
| 4,528,988 | 7/1985 | Wong . |
| 4,537,202 | 8/1985 | Mancini et al. . |
| 4,587,976 | 5/1986 | Schmid et al. ........................... 128/699 |
| 4,697,597 | 10/1987 | Sanz et al. . |
| 4,700,712 | 10/1987 | Schmid . |
| 4,850,370 | 7/1989 | Dower ..................................... 128/699 |
| 4,898,181 | 2/1990 | Kessler .................................... 128/699 |
| 4,922,920 | 5/1990 | Thie et al. ............................... 128/699 |
| 4,949,725 | 8/1990 | Raviv et al. . |
| 5,046,504 | 9/1991 | Albert et al. . |
| 5,101,833 | 4/1992 | Schmid . |
| 5,284,152 | 2/1994 | Portnuff et al. . |
| 5,458,116 | 10/1995 | Egler . |

FOREIGN PATENT DOCUMENTS

| 1526645 | 12/1989 | U.S.S.R. ................................. 128/699 |
|---|---|---|

OTHER PUBLICATIONS

Cliftan, III et al., "Direct Volume Display Devices", IEEE Computer Graphics & Applications, Jul. 1993.

*Primary Examiner*—Jeffrey R. Jastrzab
*Attorney, Agent, or Firm*—Galgano & Burke

[57] ABSTRACT

A cardiographic display for displaying an electrocardiograph heart signal in vector format within a single three-dimensional coordinate system sampled at incremental time intervals and combining the above vector display on the same screen with other displays, e.g., a 12-Lead display. Other embodiments of the present invention comprise projecting the results of the heart vectors onto three planes of the coordinate system which represent the frontal, transverse and sagittal planes while simultaneously displaying the three-dimensional vector display. Still other embodiments comprise combining the three-dimensional with various graphs which show the various changes in magnitude and angle between the heart vectors.

23 Claims, 16 Drawing Sheets
(14 of 17 Drawing(s) Filed in Color)

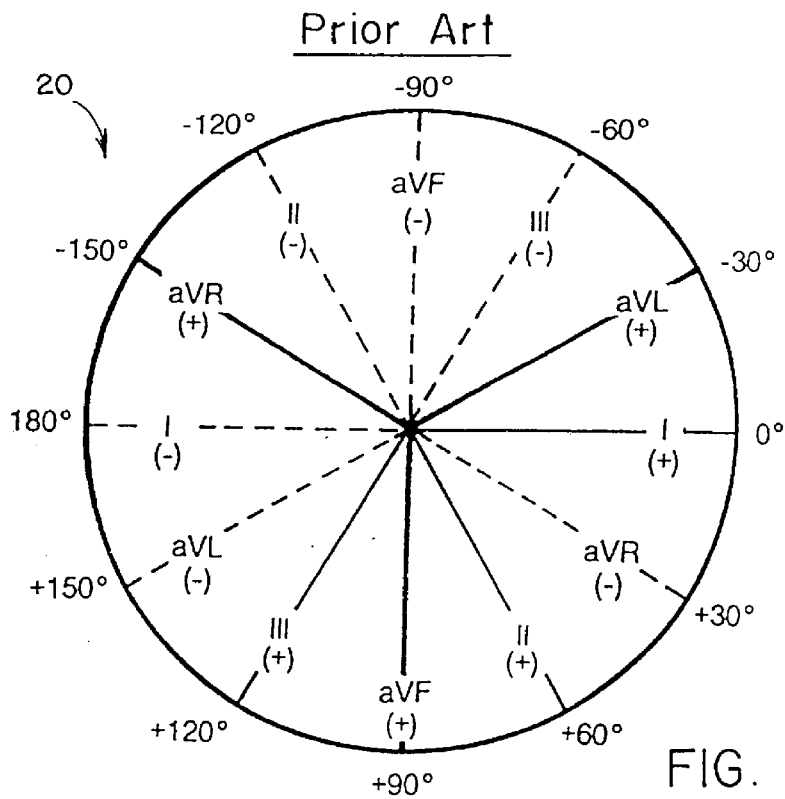
FIG. 1A  Prior Art
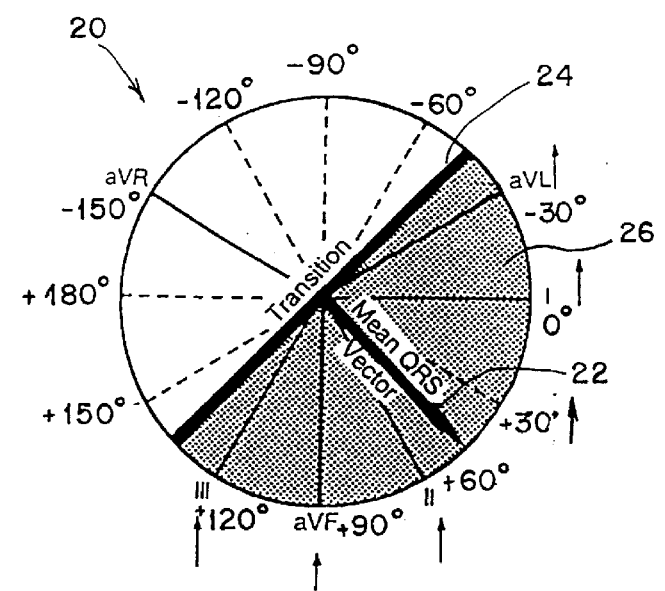
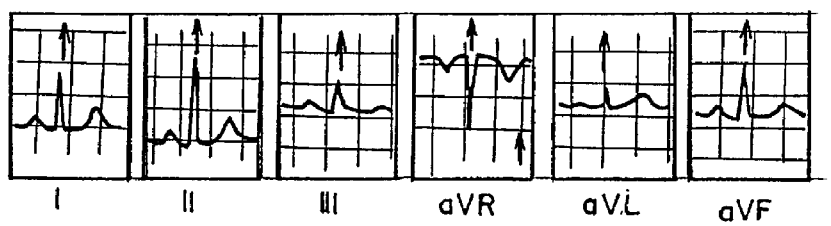
FIG. 1B

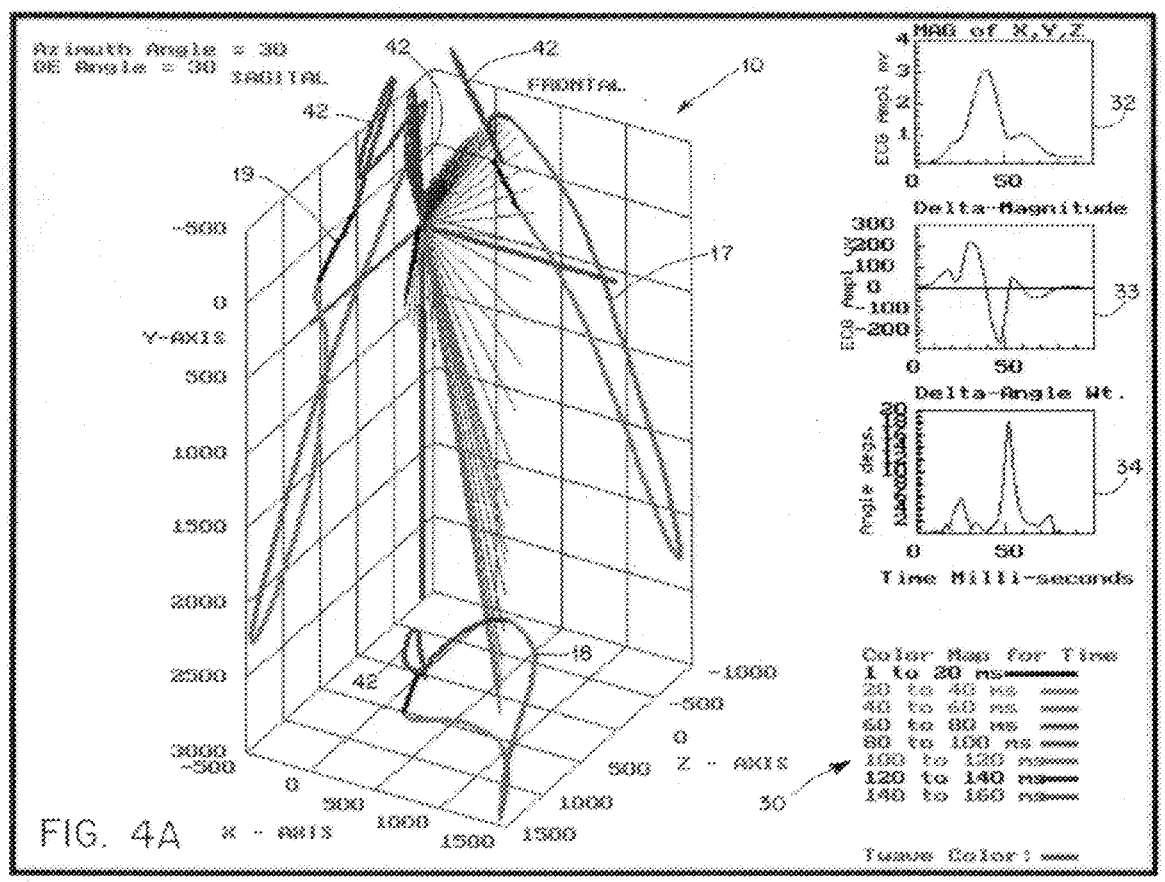

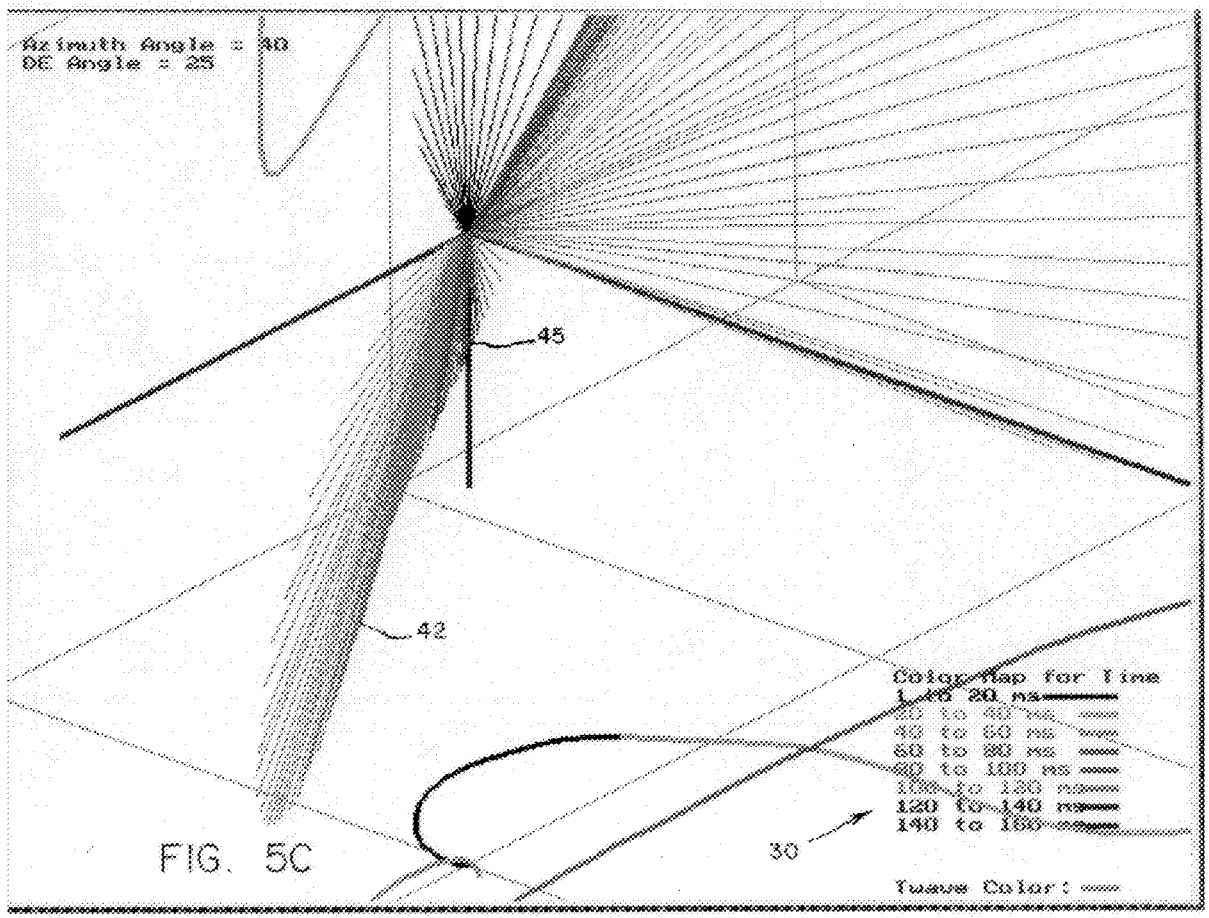

THREE DIMENSIONAL VECTOR CARDIOGRAPHIC DISPLAY AND METHOD FOR DISPLAYING SAME

The present invention relates to devices and methods for displaying the electrical signals from the heart for analysis of heart malfunctions. The present invention comprises a three-dimensional (3-D) cardiographic display which displays at intermittent time intervals electrocardiograph (ECG) heart signals as a series of vectors on a single display and in a single 3-D system which represents each of the three bodily planes, namely, the frontal, the transverse, and the sagittal planes.

BACKGROUND

Multi-lead ECGs for diagnosing various heart maladies have been used for many years. The most prevalent technique for analyzing and diagnosing heart conditions involves a 12-lead system. The 12-Lead system provides much redundant information in the frontal plane (X, Y) and transverse plane (X, Z) of the ECG vector signal. It permits only a rough visual estimate of the vector direction in theses two planes. Other techniques such as two-dimensional (2-D) vector cardiograms have proven in the past to be quite expensive and cumbersome due to the relative cost and size of the equipment needed to properly display the vector cardiograms, e.g., one cathode ray tube (CRT) oscilloscope was needed for the display of each bodily plane. Further, analysis of the 2-D vector cardiograms typically required a high degree of technical skill and mental agility in interrelating the three displays to formulate a good picture of the 3-D vector. Rules were established on the basis of individual 2-D diagrams and the 3-D vector effect was lost. As a result, the 12-Lead system has become prevalent and widely accepted.

However, in order to teach the 12-lead system, it has always been important for doctors to have a rudimentary knowledge of the relation of the ECG signal to the electrical activity of the heart. This relation is briefly summarized below.

The heart pulse is initiated by the Sino-artial (S-A) node which is generally located in the right atrium and, in a normal heart, acts as the heart's chief pacemaker. The stimulation or depolarization of the entire atria takes place after the occurrence of the S-A node pulse. A graphical representation of the initial depolarization of the atria on the electrocardiogram is represented by a positive deflection on the ECG and is commonly called the P-wave (See FIG. 12).

After an initial electrical pulse from the S-A node, depolarization of the heart muscle spreads to the atrioventicular (A-V) node and is then conducted to the "Bundle of His" (during which time it is slowed down to allow for the atrium to pump blood into the ventricles) and thereafter to the "Bundle Branches". This is known as the PR Segment. The P-R Interval represents the time of transmission of the electrical signal from the initial S-A node impulse to the ventricles.

Ventricle depolarization is known on an ECG by the QRS complex which relates to the contraction or depolarization of the heart muscles, in particular, the right ventricle and left ventricle. This is the most studied cycle and is considered to be the most important for the prediction of health and survivability of a patient. It is initiated by the signal from the Bundle of His and then the high speed Purkinje muscle fibers rapidly excite the endocardium of the left ventricle and then the right ventricle. Early experimental work showed the timing of this excitation and the progress of the electrical wave through the right and left ventricles of the heart, however, it was very difficult to determine the net vector effect of this 3-D wave had and its relationship to the overall movement of the cardiac muscle. As a result, most textbooks and physicians have adopted a simplified two-dimensional approach to analyzing this problem.

On the graph shown in FIG. 12, ventricular depolarization is clearly discernible. The most easily recognizable deflection (positive deflection—upward movement above the base line on the ECG) of the QRS complex is termed the R-wave. Just prior to this deflection is the Q-wave which is typically represented by an inverted signal deflection (negative deflection—downward movement below the base line on the ECG). The negative deflection after the R-wave is termed the S-wave which is the terminal part of the QRS complex. (See FIG. 12).

Repolarization occurs after the termination of the S-wave and starts with another positive deflection know as the T-wave. The time frame for the initiation of repolarization is termed the S-T segment and is usually represented by an isoelectric signal, i.e., neither positive or negative deflection. This S-T segment is a most important indicator of the health of the ventricular myocardium.

In order to show these electrical signals as they activate and stimulate the heart muscle, a system had to be developed to record the signals as they transverse the cardiac muscle. Einthoven found that by placing electrodes at various positions on the body and completing the circuit between the heart muscle and the electrocardiogram, it was possible to view the electrical activity between two electrodes of the heart. Each view derived from the varying placement of the electrodes was known as a "Lead". For most purposes, a typical ECG screening involves using a 12-Lead system in which the leads are arranged at various points of the body, e.g., outer extremities, and the signals are recorded across each "Lead". A physician is trained to analyze and interpret the output from these Leads and make a diagnosis. In order to help a physician make an accurate diagnosis, various formulas and methods have been developed which translate the output of the 12-Lead system into workable solutions, e.g., Einthoven's Law and 2-D Vector Cardiography.

In order to better explain the novel aspects and unique benefits of the present invention, a brief explanation of vector cardiographic analysis and the numerous steps and processes a physician typically undergoes in order to offer a somewhat accurate diagnosis is relevant.

Vector Cardiography uses a vector description of the progress of the signal through the heart during a QRS interval. This vector representation forms the basis upon which a doctor is trained to understand and explain the outputs received at the various electrodes in the 12-Lead system. Typically within a period of about 0.08 seconds (one normal QRS interval), both ventricles are depolarized and, as a result an electrical force is generated which is characterized by a vector which depicts both the size and direction of the electrical force. In electrocardiography, these vectors are created sequentially over the entire QRS interval. The normal plane for these vectors (i.e., the normal plane of activation) is the same as the QRS cycle, i.e., perpendicular to the X, Y plane (frontal) and slanted along the axis of the heart.

In actuality, the muscle depolarizes from cell to cell and forms an electrical wave front (a plane which separates tissue of different electrical potential) as a function of time. This wave front can be used to determine the resultant or mean vector whose magnitude, direction and location can be determined by the summation of all the small vectors which can be drawn perpendicular to the wave front. The resultant or mean vector of all these vectors is the resultant vector which is measured by the external electrodes and is called the QRS vector. As can be appreciated, other mean vectors are created over the other intervals in the ECG cycle in much the same manner are termed appropriately, namely, the mean T-vector and the mean P-vector.

Traditionally, it has been found that the force and direction of the QRS vector would give an accurate representation of how the heart was functioning over the period of the QRS interval. In order to help determine the QRS vector in the frontal plane, a law was developed by Einthoven which interrelated three (3) electrodes specifically oriented on the body (right arm, left leg and left arm). The signals between each two of the electrodes constituted a "Lead". These leads formed a triangle known as Einthoven's triangle and it was that these Leads could always be related to a single vector in the frontal plane, i.e., any two signals when added vectorally give a third vector. For diagnostic purposes these Leads were later graphically translated into a triaxial system. Other Leads were subsequently added to the triaxial system (i.e., termed unipolar leads—aVR, aVL, and aVF) and a Hexial system was developed. For simplification purposes, the system was displayed out on a circle and degrees were later assigned to the various leads of the system. FIG. 1a shows the circle which was developed to represent the six Leads. This system is highly redundant.

In order for a physician to determine the mean QRS vector, the physician would line up the various leads around the circle according to their positivity or negativity and mark the transition from positive to negative on the circle. This area of transition is typically referred to as the "transition" area which when analyzing a single plane, e.g., the frontal plane, is represented by a line on the circle which separates the circle into positive and negative halves. (See FIG. 1b). The mean QRS vector is positioned at a right angle to the transition line on the positive side. (See FIG. 1b).

Using the above methodology, the direction and location of the mean QRS vector on the circle determines how the heart is functioning and allows a physician to ascertain typical heart malfunctions. For example, in a normal adult, the mean QRS vector is usually located between 0° and 90°, i.e., between leads I and aVF on the circle. However, a left axis deviation (LAD) is characterized by the mean QRS vector being located in the 0° to −90° area and with right axis deviation (RAD) the mean QRS vector is located in the 90° to 180° area.

The mean T-vector and the mean P-vector are determined in a similar manner. In fact, physicians have determined that one of the more important elements of graphically illustrating the means QRS vector and the mean T-vector is that the angle between the two vectors can be easily ascertained. This angle relates the forces of ventricular depolarization with the forces of ventricle repolarization. In a normal adult, the angle between the mean QRS vector and the mean T-vector is rarely greater than 60° and most often below 45°.

Similarly, the mean P-vector can be determined. This enables a physician to isolate the location of the electrical direction of the excitation of the cardiac muscle of the atrium.

The above analysis has been described using a single plane, namely the frontal plane characterized by the superior, inferior, right and left boundaries of the human body. In order for a physician to analyze the overall movement of the heart muscle during depolarization and repolarization, the physician needs to analyze the vector forces along another plane, namely the horizontal plane which is characterized by the posterior, anterior, right and left boundaries of the human body.

Much in the same manner as described above, six leads are positioned about the body to measure the electrical currents across the heart muscle in the horizontal plane. These leads are typically called the precordial leads and are represented as VI–V6, respectively. Using the same methodology as described above with respect to the frontal plane, the location and direction of the mean QRS vector in the horizontal plane can also be determined.

When the two planes are analyzed simultaneously, the mean QRS vector (and the other vectors) projects perpendicularly from the transition "plane" rather than the transition "line" of the single plane system. In other words, when the frontal plane and the horizontal plane are isolated and individually analyzed, the mean QRS transition appears as a line across the diameter of the circle. In actuality this "line" is actually a "plane" when both systems (frontal and horizontal) are analyzed simultaneously and the mean vectors (QRS, T and P) project perpendicularly from this plane into both systems.

As can be appreciated from the above summary, the analytical process of determining the resultant QRS vector and the other vectors can be quite cumbersome and requires a physician to interpret various graphs and/or solve various formulas which tend only to frustrate the diagnostic process and which can lead to erroneous conclusions if analyzed improperly. For simplicity, most physicians analyze each system individually at first and then combine the results. However, as often is the case, the determination of the mean vectors (QRS, T and P) in one plane is still both tire consuming and somewhat confusing. Further, trying to determine how the mean vectors project into two planes and how the angles between the vectors relate can be even more confusing.

Moreover, even if a physician can adequately analyze the various graphs and solve the various formulas to arrive at a diagnosis, three-dimensional representation of the location of the mean QRS vectors (and the other vectors) must be mentally visualized which requires a high degree of mental agility and can lead to misdiagnosis. Further, mentally visualizing the angles between mean vectors would be virtually impossible for even the most skilled physician. The additional problem of how these vectors change in time over the QRS interval is believed to be nearly impossible to consider by the prior methods.

In the past, several attempts have been made at resolving the above problems. For example, 2-D vector cardiograms isolated the various signals from the leads and used several oscilloscopes to show the results in three planes (frontal, transverse (horizontal) and sagittal). This has been studied in great detail and many texts have been written to relate these diagrams to various heart maladies. However, as far as is known no one has ever attempted to display the signal as a series of 3-D vectors plotted at intermittent time intervals over the duration of the signal, much less represent these vectors on a single display and on a single 3-D coordinate system thereby producing a more easily identifiable 3-D view of the 12-Lead ECG signal or QRS complex as it progresses through the cardiac muscle over time.

It would therefore be desirable to provide a device which can overcome many of the aforesaid difficulties with diagnosing and analyzing heart malfunctions and provide devices and methods which display heart maladies in an easily recognizable and distinguishable manner allowing even an untrained observer to easily visualize, isolate and analyze common heart conditions.

SUMMARY OF THE INVENTION

Accordingly, it is an object of the present invention to provide a novel device and method which uses a vector description of the progress of the signal through the heart during the QRS interval which forms the basis upon which the doctor is trained to understand the outputs received at the various electrodes in the 12-Lead system.

While apparently generally acceptable for their intended purposes, so far as is known, none of the prior art devices display an electrocardiograph heart signal in vector format within a single three-dimensional coordinate system sampled at incremental time intervals which comprises a point of origin and a three-dimensional coordinate system comprising an x-axis, a y-axis and a z-axis extending from said point of origin.

The present invention further comprises a frontal plane defined by the area between the x-axis and the y-axis, a sagittal plane defined by the area between the z-axis and the y-axis and a transverse plane defined by the area between the x-axis and the z-axis. The invention further comprises a displaying mechanism which displays the magnitude and location of the signal within the coordinate system at incremental time intervals using a plurality of vectors, the displaying mechanism emanating from the point of origin.

The present invention also provides new three dimensional cardiographic display and method for performing the same which displays the orthogonal X, Y and Z axis outputs from multiple Lead, e.g., 12-Lead or "Frank" configuration of electrodes (seven Lead system whereby the electrodes are placed at specific positions on the body to provide an X-axis pair, Y-axis pair, a two axis pair and a ground reference lead to minimize interference), in vector format on a single display at millisecond time intervals. It is also an object of the present invention to provide a device which interprets the sampled data from an ECG digitally recorded signal at certain time intervals and projects this signal as a vector from a point of origin to a point in 3-D space as related to the X, Y and Z axii.

The present invention eliminates the step-by-step analytical process explained above typically involved with diagnosing heart conditions and provides a new display that is intended to enhance recognition of the presence and type of malfunctions related to the cardiac muscle.

Another object of the present invention, is to provide a novel display which integrates other information about the heart onto the same display which it is believed will further enhance diagnostic analysis, e.g., displaying the 12-Lead output as related to the vectorgrams to provide a reference for doctors that are trained in this technology; a calibrated display of the magnitude of the vector (Magnitude= squareroot ($X^2+y^2+Z^2$)) for easier evaluation of hypertrophy and possibly other conditions; displaying the change in Magnitude from one vector to the next, which is believed to be an indication of the continuity of heart muscle cell activation and an additional indicator of disease; and displaying the change in the angle of the heart vectors over the same time interval which is believed to be a further indicator of muscle cell activation and smoothness of transition of the depolarization of cells over the myocardium.

Embodiments of the present invention project the results of the 3-D heart vectors onto three planes, namely, the frontal, the transverse find the sagittal planes, which it is believed will further enhance the interpretation of the vector presentation.

Embodiments of the present invention distinguish the vectors sequence over the QRS cycle, e.g., by color coding the time of occurrence of the events in the QRS cycle, the ST offset, and the T-wave tc clearly show their interrelationship and timing, so important to the recognition of normal versus diseased conditions.

Further embodiments of the present invention allow a physician or medical technician to manipulate the vector display to facilitate more detailed examination of any portion of the vector sequence as a function of time, e.g., the vector display may be expanded or magnified to highlight and allow closer examination of certain areas; the vector display may be shifted in steps both horizontally and vertically from its present location; the vector display may be rotated about the vertical axis 360 degrees, and elevated or declined about the X-axis in steps; and the T-wave, P-wave or other portion of the display may be removed if it interferes with the observation of other portions of the signal.

Embodiments of the present invention show and highlight on the display, e.g., by (color or other means, the magnitude and direction of the ST voltage offset, if any.

These and other aspects of the present invention are described in greater detail below.

BRIEF DESCRIPTION OF THE DRAWINGS

The file of this patent contains at least one drawing executed in color. Copies of this patent with color drawing (s) will be provided by the Patent and Trademark Office upon request and payment of the necessary fee.

In the drawings, wherein similar reference characters denote similar elements throughout the several views:

FIG. 1a is an illustration of the Hexial System showing the six leads in the frontal plane;

FIG. 1b illustrates how the six Leads, I, II, III, aVR, aVL and aVF are translated onto the Hexial System of FIG. 1a to graphically depict the mean QRS Vector, the Transition Line, and the positive side of the Transition Zone;

FIG. 4a is a 3-D vector cardiographic display of a heart with left ventricular hypertrophy;

FIG. 5c is a highly enlarged view of the 3-D vector cardiographic display of FIG. 5a highlighting the ST vector in the color red;

DETAILED DESCRIPTION

One embodiment the present invention comprises a cardiographic display for displaying an electrocardiograph heart signal in vector format within a single three-dimensional coordinate system sampled at incremental time intervals which comprises a point of origin and a three-dimensional coordinate system comprising an x-axis, a y-axis and a z-axis extending from said point of origin. This embodiment further comprises a frontal plane defined by the area between the x-axis and the y-axis, a sagittal plane defined by the area between the z-axis and the y-axis and a transverse plane defined by the area between the x-axis and the z-axis. The invention further comprises a displaying mechanism which displays the magnitude and location of the signal within the coordinate system at incremental time intervals using a plurality vectors, the displaying mechanism emanating from the point of origin.

Turning now to the drawings, and in particular FIG. 1a, therein illustrated is a graphical representation of a circular Hexial system 20 illustrating the six leads of the frontal plane positioned at various degrees on the circle relating to their positivity and negativity. Leads I, II and III are commonly termed the "bipolar" extremity leads and leads aVR, aVL, and aVF are commonly termed the "unipolar" leads. For simplicity purposes, most textbooks teach these leads arranged at 30° increments around the circle which makes the actual diagnosis somewhat less burdensome but also less exact.

FIG. 1b illustrates how a physician would use the circular Hexial system 20 to incorporate and relate the signals from the six Leads to determine the QRS Vector 22, the Transitional Line 24 and the positive area of the Transitional Zone 26. This analytical process is described in detail above.

Figure 2A:
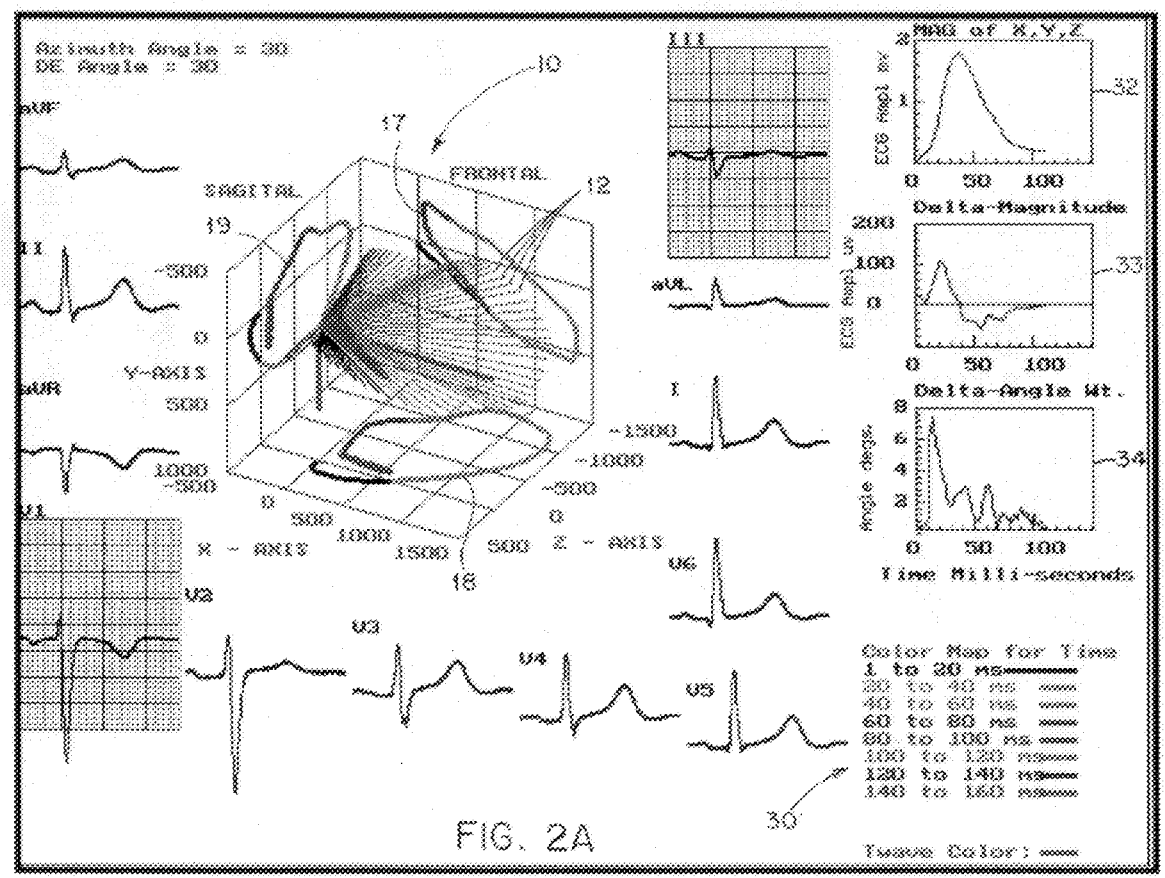
FIG. 2a is a 3-D vector cardiographic display of a normal heart shown with several accompanying displays on a single screen.
Figure 2B:
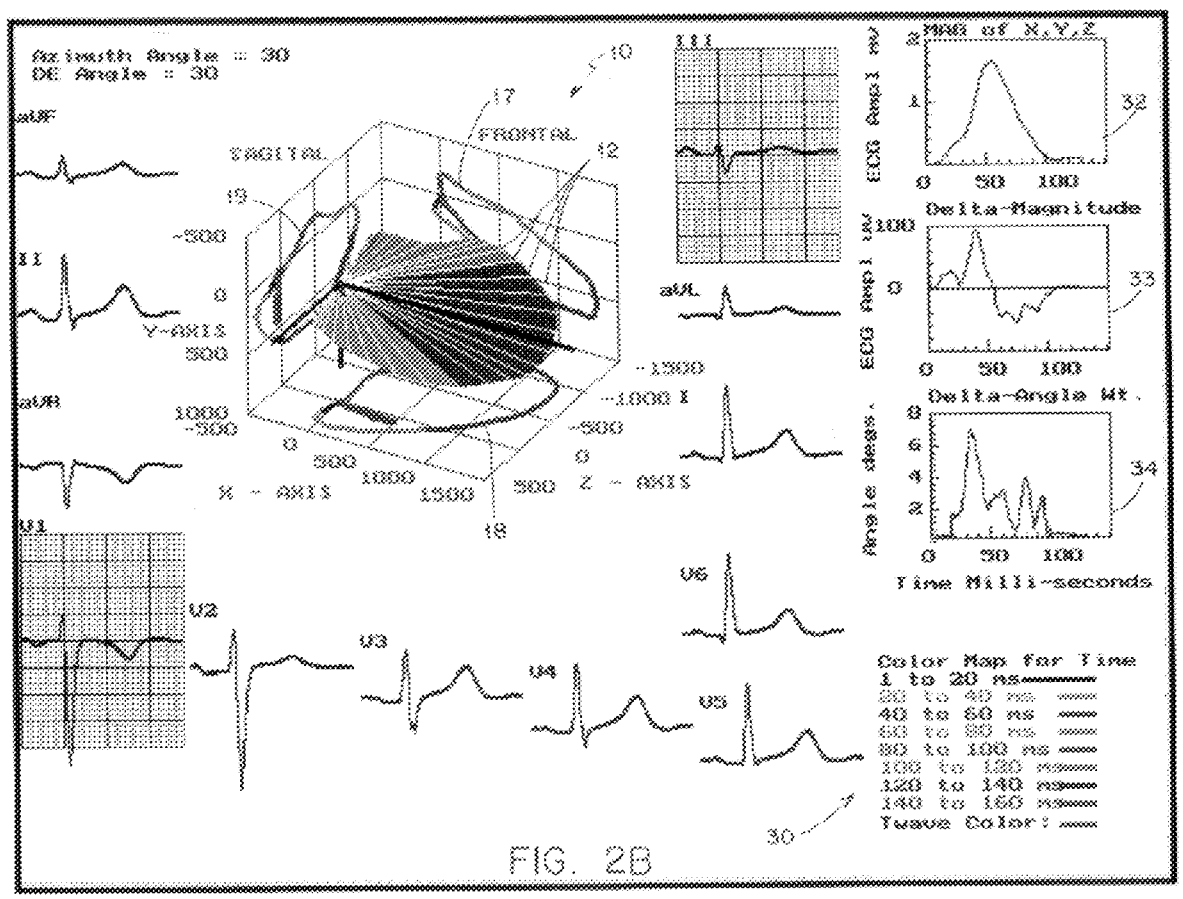
FIG. 2b is the 3-D vector cardiographic display of FIG. 2a showing the integration of surface modeling techniques between vectors.

FIGS. 2a and 2b show an example of a 3-D vector cardiographic display 10 of the QRS interval of a normal heart. In this particular case, the heart vectors 12 for the QRS interval are determined at 1 ms intervals. The vectors 12 are color-coded over 20 ms time intervals so the sequence of the vectors 12 over the entire QRS interval can be easily discerned. The color coding sequence or map 30 can be selectively displayed by a physician when needed.

It is believed hat displaying the heart vectors 12 in this novel fashion enables a physician to visually perceive critical information for the diagnosis of heart disease. Displaying the heart vectors 12 in this fashion also provides a good visual clue as to the plane of the vectors 12 over the entire QRS interval, which is also important for diagnosing heart disease. It is also much Easier to interpret the results of a 3-D vector representation, since it relates directly to the orientation of the heart in the body, and the deviation from a normal pattern becomes immediately obvious even to the untrained observer.

FIG. 2a also combines the standard displays of the 12-Lead system, the 2-D vectorgrams and the 3-D vector display. Preferably, the accompanying displays do not interfere with the 3-D vector display 10 and are generally positioned at various locations around the display 10. For example, in FIG. 2a the various Leads from the 12-Lead system are positioned around the 3-D vector display in a general counterclockwise manner starting with the aVF lead at the upper left corner of the display 10 following to the III lead at the upper right corner of the display 10. Preferably, it is possible for a physician to selectively manipulate any or all of the lead displays or other accompanying displays to various positions on the screen. Other accompanying displays can include various graphs 32, 33, 34 representing, e.g., the changes in magnitude and angle of the heart vectors and/or a display of the color map for readily distinguishing the various vectors.

As can be appreciated from the present disclosure, a physician can selectively determine which display he wants to view at any particular time during the diagnosis. Further, it is within the scope of the present invention to allow a physician to selectively manipulate, e.g., magnify (zoom in), color, or rotate any one of the displays at any given time. Although the 3-D vector display 10 is believed to be far superior than the other displays, by combining the 3-D vector display 10 with theses other displays on a single screen, it is believed that most, if not all, known heart conditions can be readily observed. For example, by also projecting the results or terminal points of the vectors 12 simultaneously onto each of the three respective planes (frontal, transverse and sagittal) of the 3-D vector display thereby forming 2-D vector cardiographic projections 17, 18 and 19 on the same screen as shown in FIGS. 2a and 2b, it is much easier for a physician to visualize conditions that may be hidden on the 3-D display 10 without rotating or expanding the display 10.

FIG. 2b illustrates the normal heart of FIG. 2a with the spaces between vectors 12 filled and/or shaded. Preferably, theses spaces are color mapped in a manner similar to the vectors. Advantageously, surface modeling and hidden line representation techniques are employed to further enhance the picture.

Figure 3:
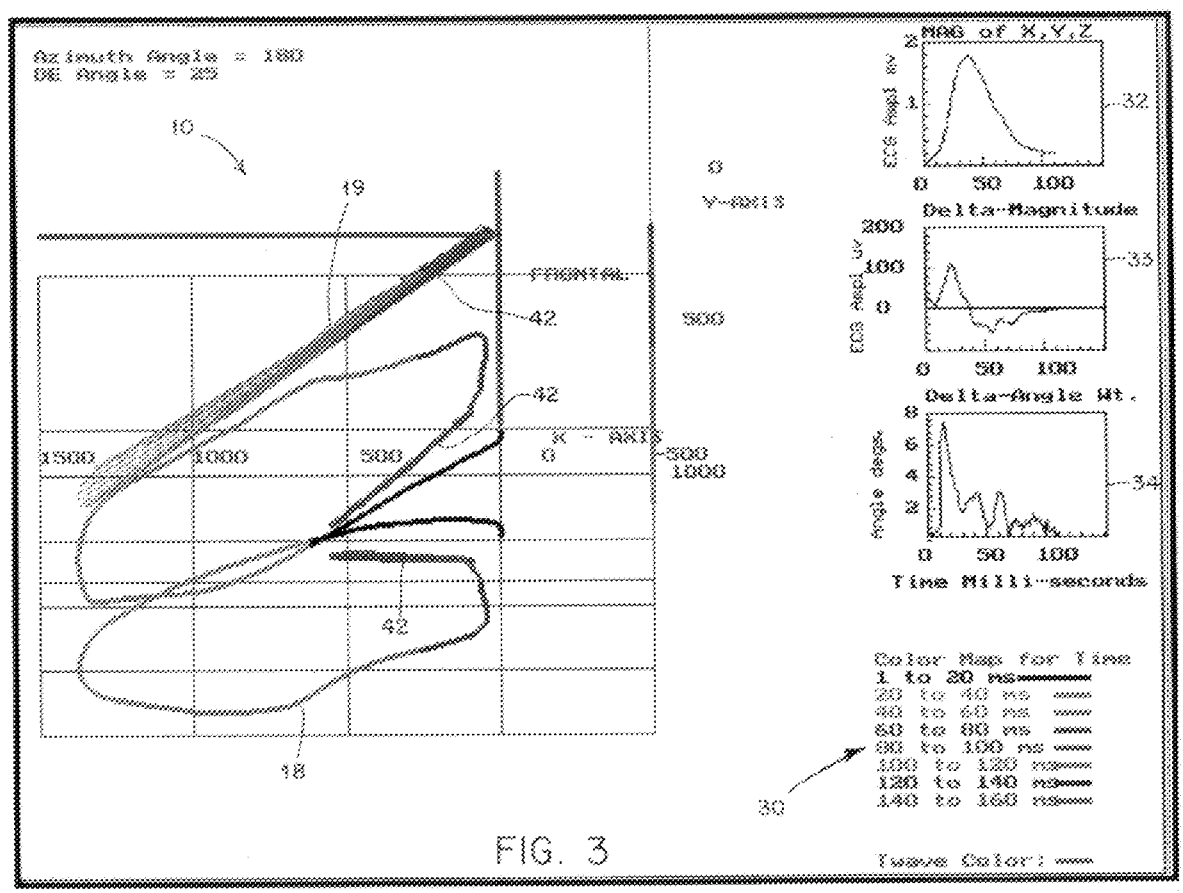
FIG. 3 is a 3-D vector cardiographic display of a normal heart of FIG. 2 at a 180° azimuth showing the slant of the plane of heart vectors.

FIG. 3 shows the normal heart of FIG. 2 which is rotated about a 180° azimuth. As can be appreciated from the present disclosure, a physician is able to manipulate the 3-D vector cardiogram 10 for viewing purposes. For example, by rotating the vector display of FIG. 2, it is possible to observe that the vectors 12 fall within a single plane. The angle of this plane can be easily measured as an indicator of the orientation of the axis of the heart in the body. As can be appreciated from the present dis closure, the 3-D vector cardiogram 10 can be manipulated in many fashions to view or highlight certain aspects of the display, e.g., the T-wave 42 can be readily observed as being oriented along the same axis as the main axis of the QRS complex which characteristic of a normal heart.

Figure 4B:
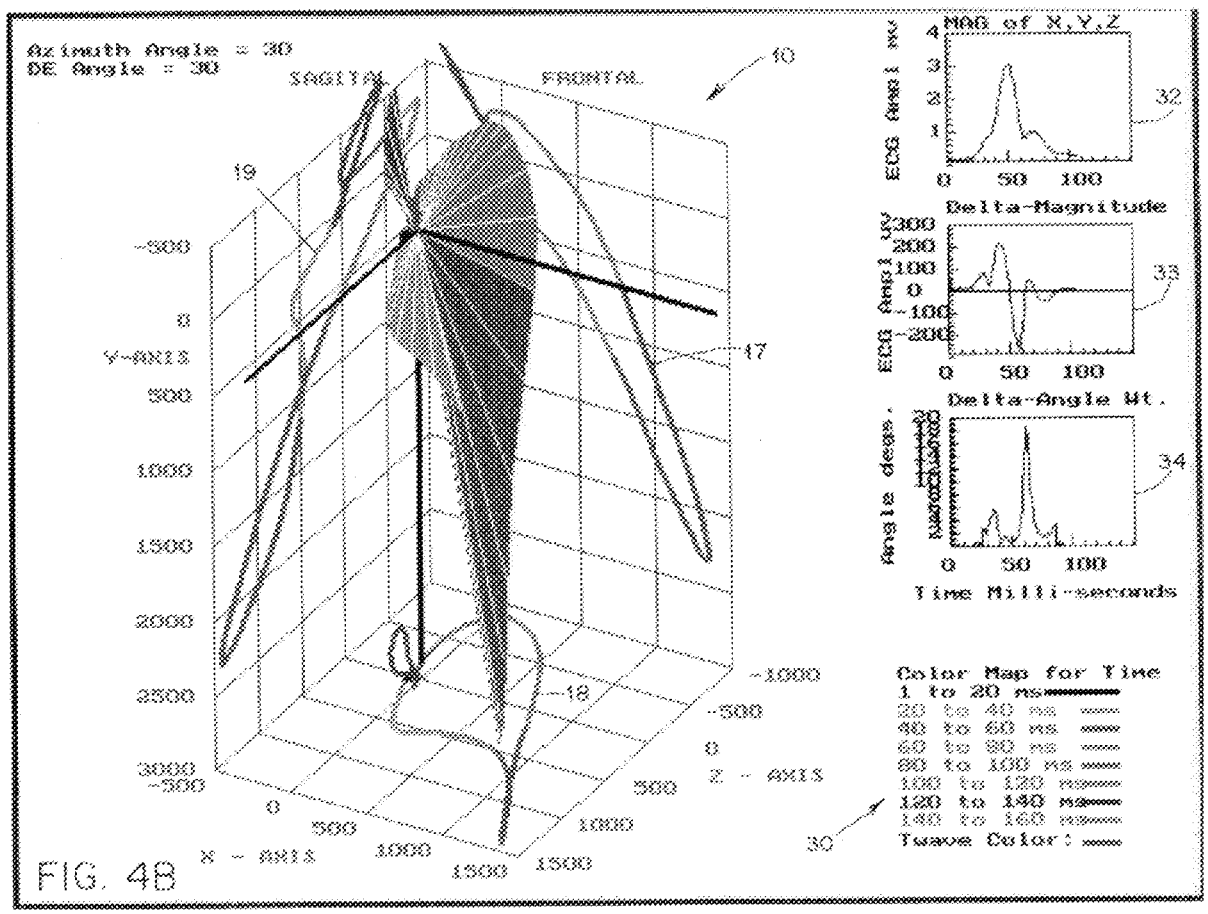
FIG. 4b is the 3-D vector cardiographic display of FIG. 4a showing the integration of surface modeling techniques between vectors.

In contrast to this normal heart we show the case of a heart with hypertrophy—i.e. enlarged heart muscle—shown in FIGS. 4a and 4b. The QRS complex starts out in a normal manner over the first 25 milliseconds, then the magnitude increases very rapidly to a maximum of 3 millivolts. As can be appreciated, an abnormal condition is easily and immediately discernible which was not necessarily the case with displays of the past.

In the case of FIG. 4a, the vector direction of this maximum (anterior, inferior and left) and its time of occurrence could indicated a enlargement of the muscles in the apex of the heart. Diagnosis is left ventricular hypertrophy. Other parts of the ECG signal and their respective locations and directions over the time interval can also be easily and immediately identified. For example, in FIG. 4a, the T-wave 42 is in the reverse vector direction of the main axis of the heart, which is also an indicator of hypertrophy. FIG. 4b illustrates the same heart using surface modeling and hidden line techniques.

As can be appreciated from the present disclosure, the size, shape and smoothness of this vector plane allows a doctor or technician to immediately determine whether the patient has a healthy or unhealthy heart, thereby expediting the task of making a proper diagnosis. For example, if the display shows colors that represent intervals of time over 100 ms, a physician will immediately know that there is a problem, e.g., "Bundle Branch Block". Further, if the physician observes that the plane of the heart vector diagram is split into two planes, or, if the plane is above, the x-axis, again, the physician immediately recognizes that there is a problem which is believed to be a myocardium infarction (as related to coronary heart disease). As can be appreciated from the present disclosure, more analysis of the 3-D vector cardiographic display may identify any number of other maladies more quickly that conventional methods and may more accurately recognize maladies previously unobserved. It is believed that a extensive medical evaluation may be needed to determine the statistical limits of the present invention for diagnostic purposes.

The vector direction of the T-wave 42 is important for diagnostic purposes and, as can be appreciated, is immediately apparent from the various figures, in particular, FIG. 4a. If the T-wave 42 points in the opposite direction to the main body of the QRS, a problem is indicated. Its direction is indicative of the location of infarction or ischemia that exists in the diseased heart, i.e. anterior, lateral, inferior, or posterior or combinations of these. The P-wave (not shown) can also be integrated into the display (in a similar manner as the QRS interval). This P-wave has diagnostic potential for functions of the atrium of the heart, e.g., the initial electrical pulse form the S-A node, ard careful study of the P-wave when displayed in the manner of the present invention may enable a physician to easily pinpoint the location and/or problems with the atrium.

It is believed that the display of the vectors 12 in small time intervals, e.g., from about 0.5 ms to about 10 ms, provides potential for diagnosing early signs of potential for ventricular fibrillation and/or Ventricular tachycardia (VT). In has been seen in some of the cases which exhibit severe myocardial infarction that the vectors 12 over these regions are very irregular, i.e., the changes in magnitude and angle of the vectors are not smooth. Studies of the movement of the excitation of heart muscle cells in the region of infarction show that barriers exist to the smooth conduction of muscle excitation. Several of the illustrated cases of the present invention display these effects, namely, the fluctuation of these vectors, which can be seen from their spatial irregularity.

As mentioned abc)ve, additional displays 32, 33 and 34 can also be selectively combined with the 3-D vector cardiograph 10 to show the amplitude and angle fluctuations between successive vectors 12 of the 3-D display 10. These displays 32, 33 and 34 are a measure of the smoothness of the vector 12 motion and may provide additional information of the degree of damage that may exist in the heart muscle. The displays 32, 33 and 34 are calibrated in time with the QRS interval and thus can be readily associated with the 3-D vector display 10 to identify areas of roughness.

The magnitude of the vectors 12 calibrated in time over the QRS interval is selectively displayed by graph 32 as seen in several of the illustrations, e.g., FIG. 2a. This provides a good measure of the maximum amplitude of the heart signal which is an important tool in the diagnosis of left ventricular hypertrophy. In the case of the 12-Lead system, it is necessary to add the levels from a number of the electrodes in order to gain an idea of this amplitude, whereas this graphic display gives a direct unambiguous measure.

Display 33 shows the change in magnitude between successive vectors. It is believed that this change is a measure of the smoothness of the traveling of the muscle cell excitation wave front through the myocardium. Erratic changes are an indication of disrupted or infarcted tissue and thus provides a qualitative indication of tissue health. Since this is a new display concept, it may require additional evaluation before it can be used diagnostically.

Display 34 shows the change in angle between successive vectors. This is another measure of the character of the muscle cell excitation wave front. This display reveals erratic changes which is believed to be indicative of diseased tissue. This display also shows rapid and fast changes in vector direction which it is believed is indicative of the end of muscle excitation in one region of the heart and transfer to another region. Much like display 33, this is believed to be a new display concept and may require thorough evaluation.

Figure 5A:
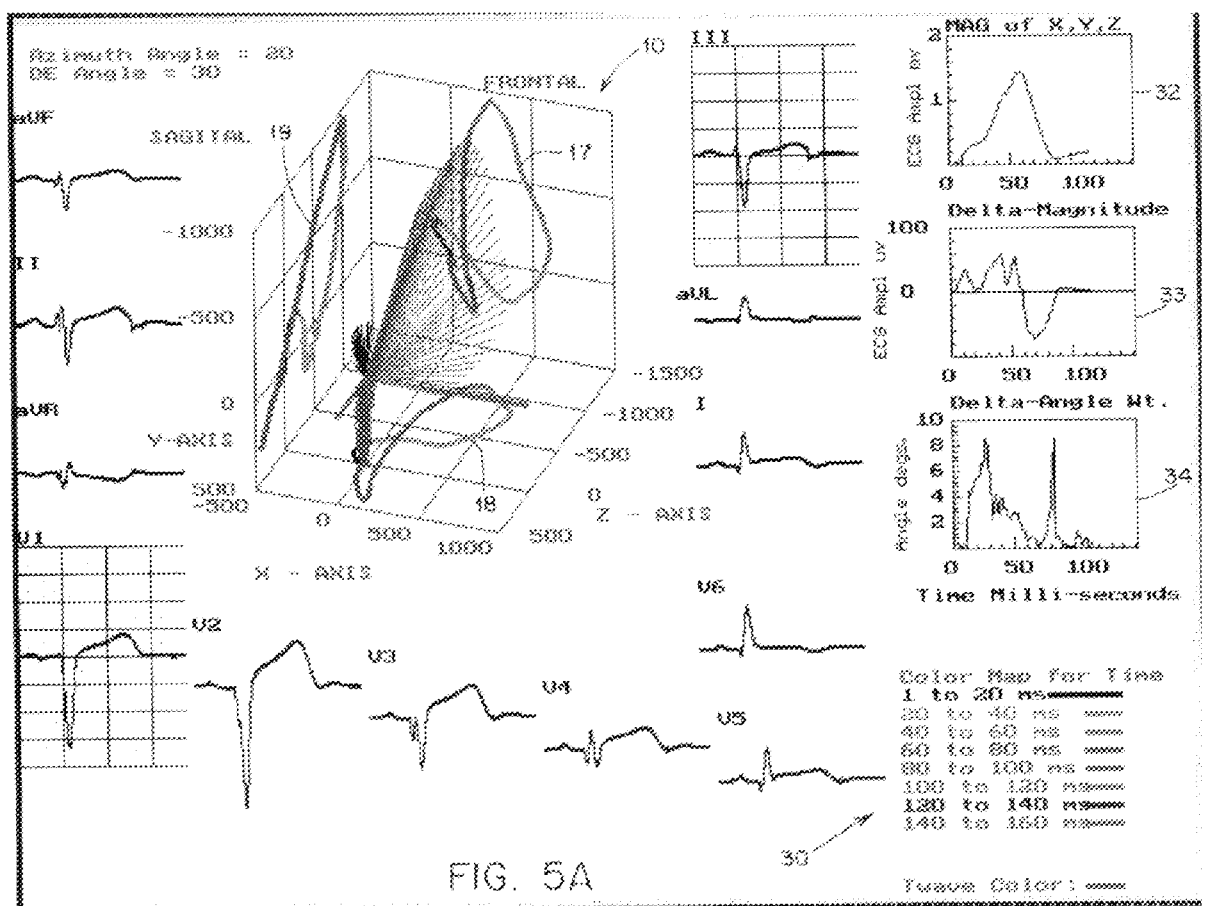
FIG. 5a is a 3-D vector cardiographic display of a heart showing anterior/inferior infarct along with several accompanying displays.
Figure 5B:
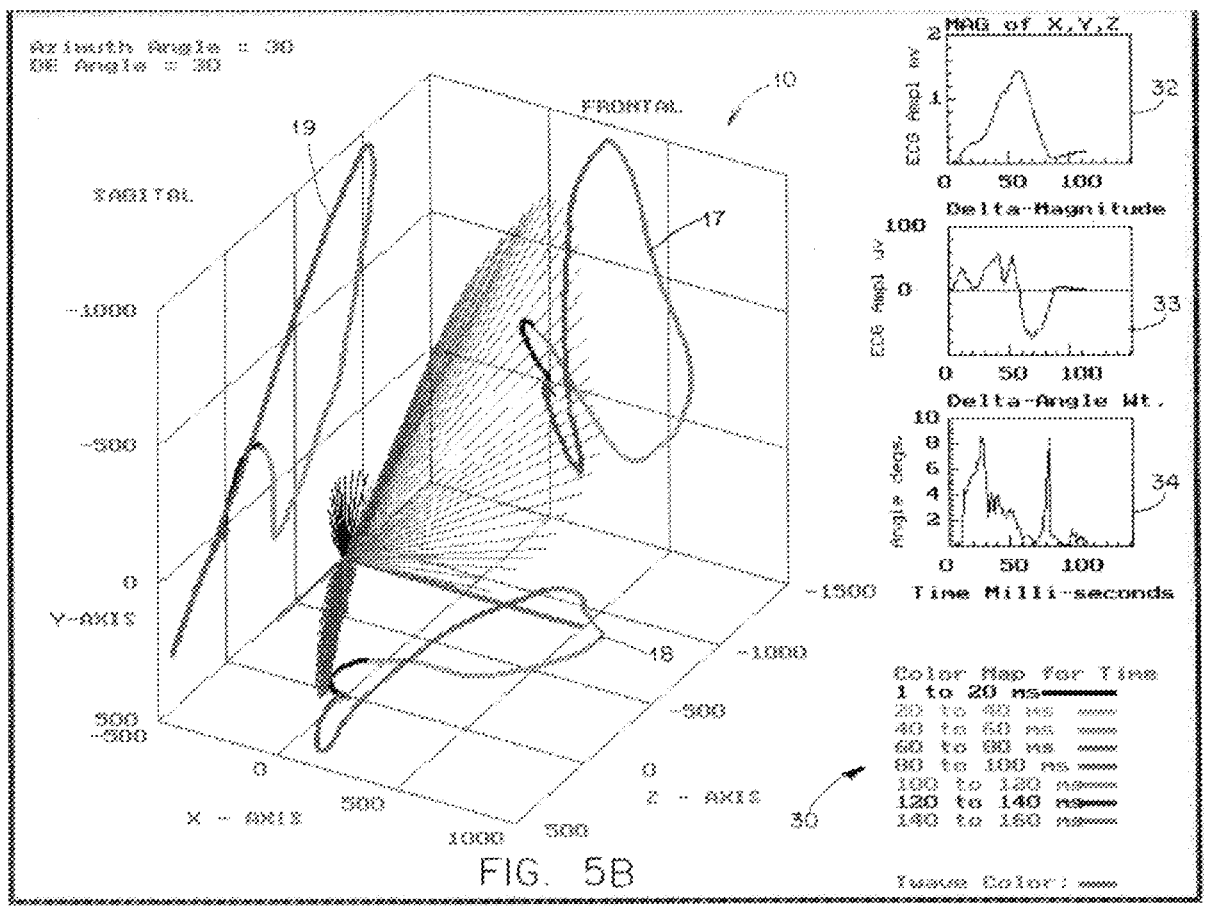
FIG. 5b is an enlarged view of the 3-D vector cardiographic display of FIG. 5a shown without the 12-Lead displays.

Another illustration of heart disease is shown in FIG. 5a. In this case there is definite indication of anterior heart disease. This has been diagnosed from the 12-Lead data that is shown. The deviation of the vector diagram 10 is also clearly shown. The initial vector direction is right, then posterior, then a progression towards the left, followed by a large increase to the posterior, superior direction. This is shown in FIG. 5b and FIG. 5c in larger display. The entire diagram could be produced by taking a normal heart vector diagram and adding a vector in the opposite direction of the anterior and inferior region of the heart whose vectors are not being generated due to a loss of function. When the QRS is completed it does not return to zero but has an offset. This offset can be incorporated into the 3-D display via an additional vector 45 (color coded in bright red) as seen best in FIG. 5c. This vector represents the end of the QRS interval and the very beginning of the ST interval. It is believed that this vector 45 can be useful in the diagnosis of the location of ischemia or infarction. As depicted by vector 45 in FIG. 5c, the magnitude and direction of the ST voltage offset, if any, is easily recognizable on the display because it is distinguished in color. In addition, it is believed that the position and orientation of the vector 45 offset is useful for determining the location in the heart of the failure, such as the coronary artery that is blocked, e.g., the direction of the vector 45 points to the location of the ischemia. The magnitude of this vector 45 is also useful since it has been seen to relate to a recent ischemic episode. For example, in the case illustrated in FIGS. 5a–5c, the vector 45 points to the anterior and inferior location, which confirms the original diagnosis from the direction of the disturbed QRS vector diagram. As can be appreciated from the present disclosure, other indicators than color may be employed to distinguish vector 45 or any other vector 12, e.g., shading and/or varying the line weight and type.

Figure 6:
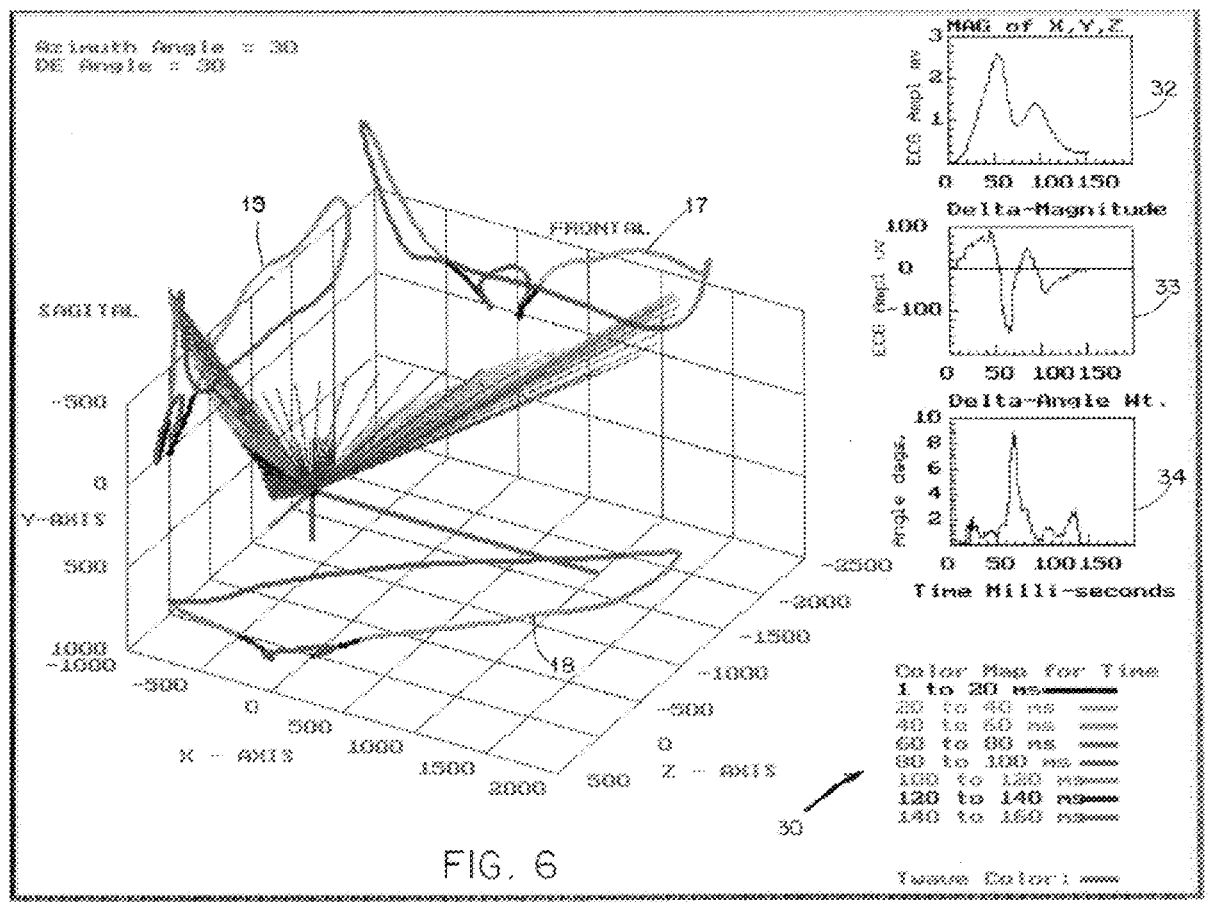
FIG. 6 is a 3-D vector cardiographic display of a heart showing left bundle branch block.

Another case is shown in FIG. 6 of a patient with LBBB (Left Bundle Branch Block). This illustration shows the large amount of detail that is available from the vector display 10 concerning the sequence of excitation of the heart muscle in these cases. In the case of LBBB the right ventricle is excited first by the Purkinje right bundle. The muscle cells then conduct the depolarization process to the left ventricle. The paths established in this manner are different from the case of normal excitation. As a result, the vector diagram is different from the normal case (See FIGS. 2a, 2b and 3) as is obvious from the appearance of the display 10. One result which is immediately perceivable is the fact that the duration of the QRS signal is much longer than the normal QRS process, which is the first criteria for BBB—i.e. the QRS complex is longer than 110 ms. It is believed that there may be much more that can be read from this display after careful study and analysis, e.g., the potential for allowing diagnosis of infarction in the presence of LBBB.

It is also possible to apply the 3-D vector display 10 to data taken in real time. FIGS. 7–11 shows some examples as a series of 3-D cardiograms shown from real time QRS and T-wave data shown for a normal heart. These were consecutive heart cycles and are interesting for the possible assessment of changing vector 12 characteristics from beat to beat as may be the case for ischemic or infarcted tissue.

Figure 7:
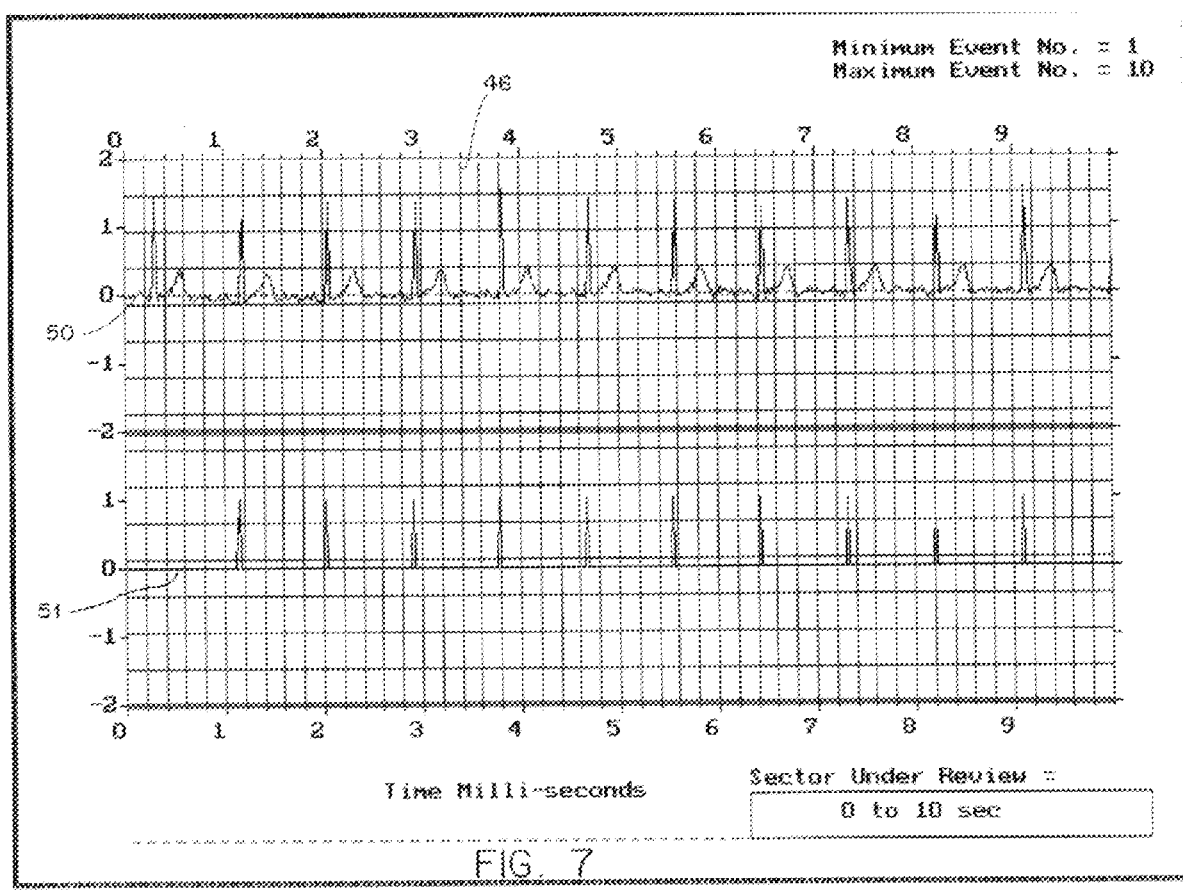
FIG. 7 is a graphical display of a series of detectors of events over 10 seconds for selection of a real time event to be displayed in 3-D vector cardiographic format.
Figure 8:
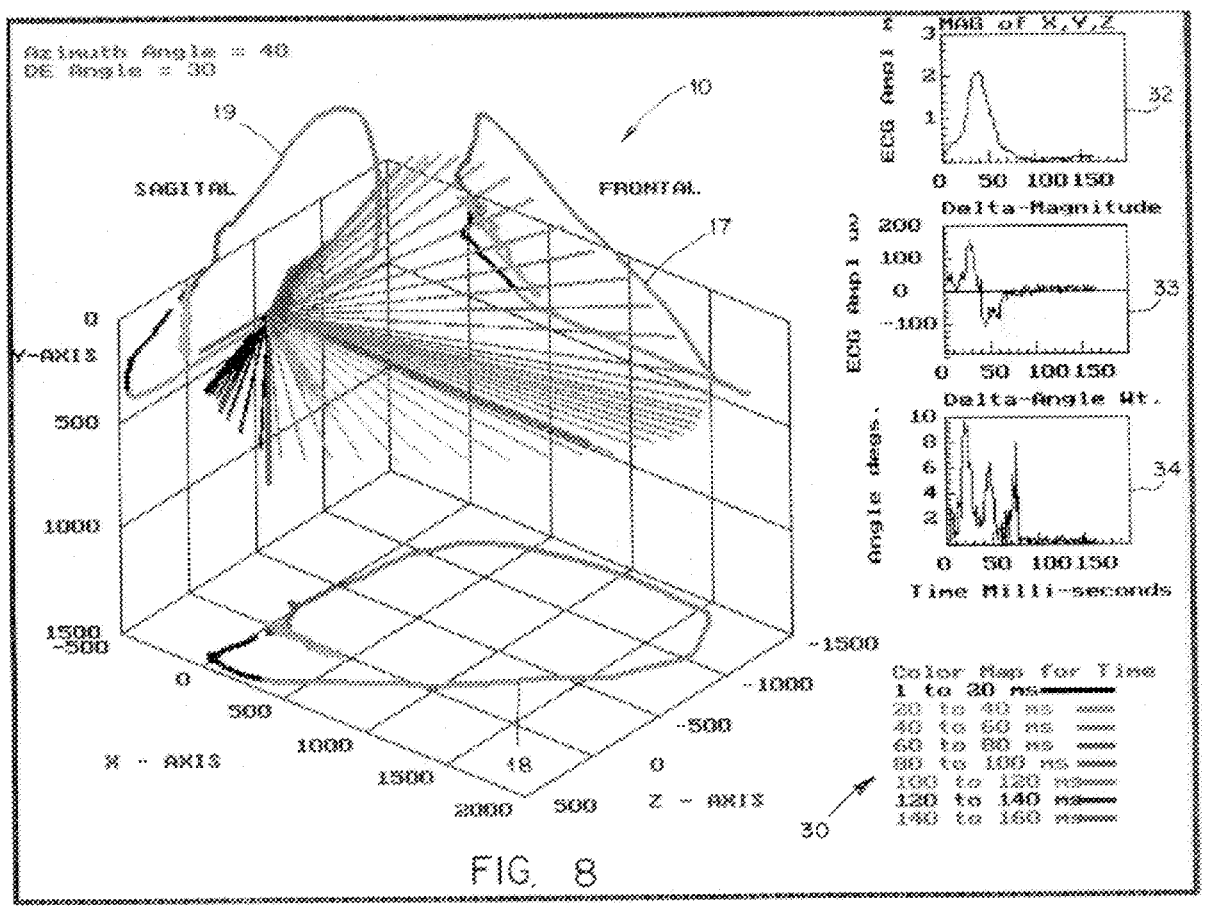
FIG. 8 is a 3-D cardiographic vector display of event No. 6 of FIG. 7.
Figure 9:
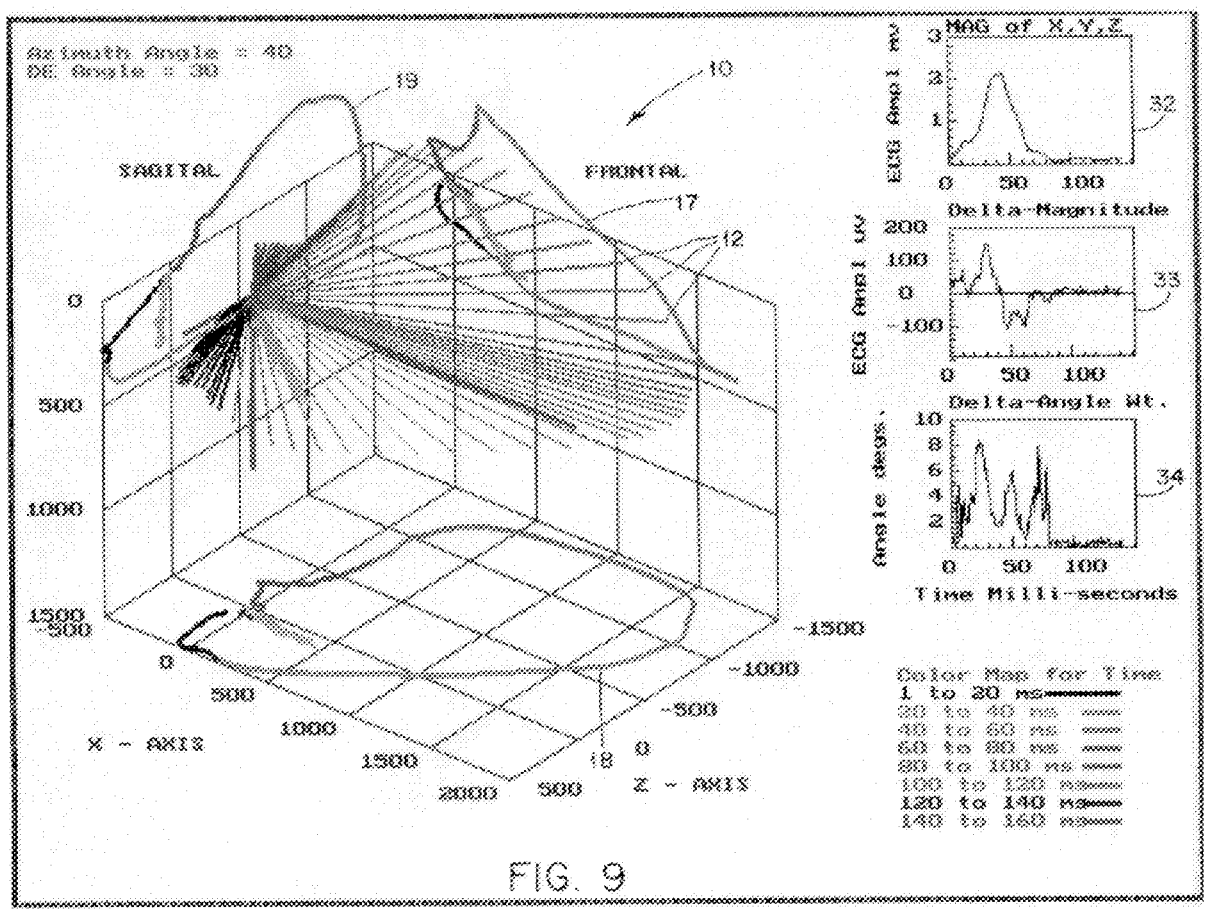
FIG. 9 is a 3-D cardiographic vector display of event No. 7 of FIG. 7.
Figure 10:
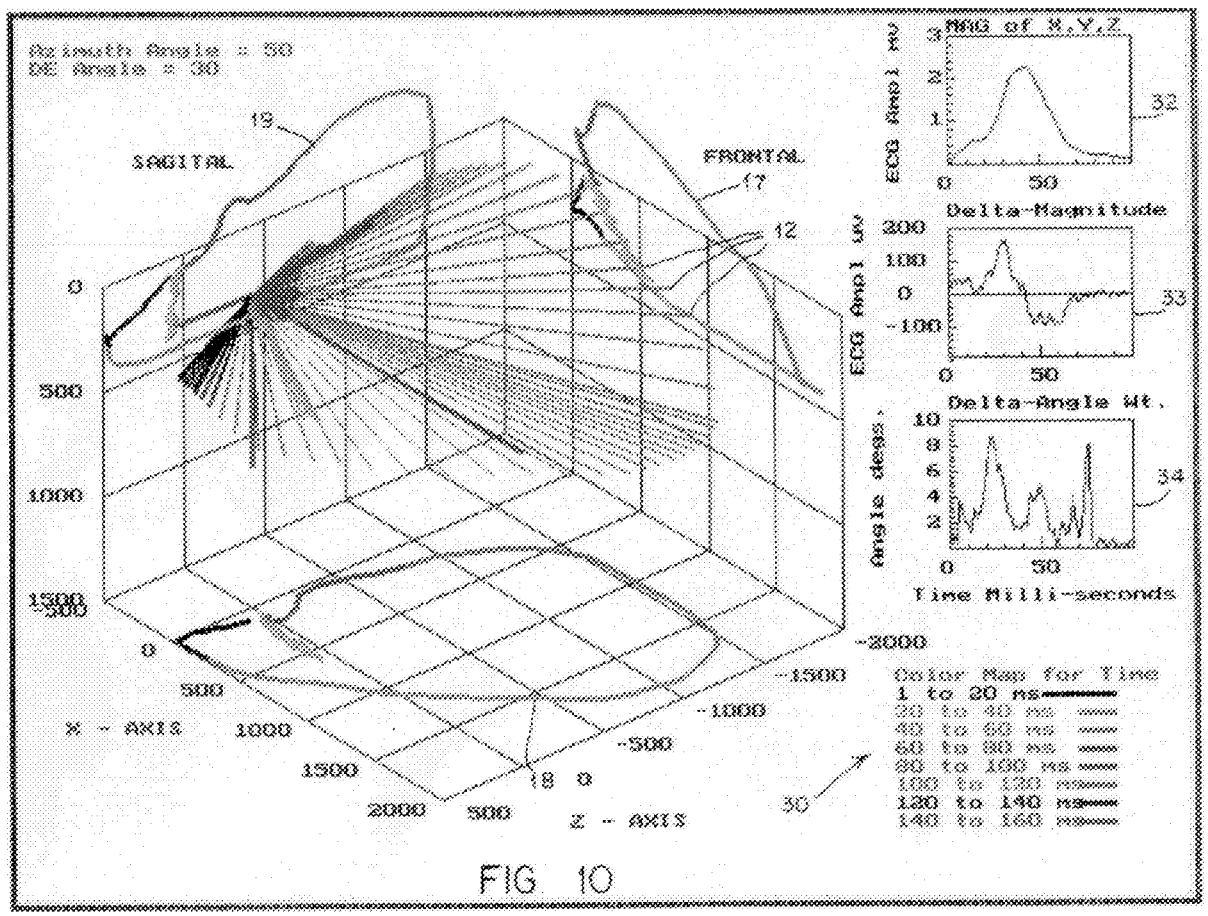
FIG. 10 is a 3-D cardiographic vector display of event No. 8 of FIG. 7.
Figure 11:
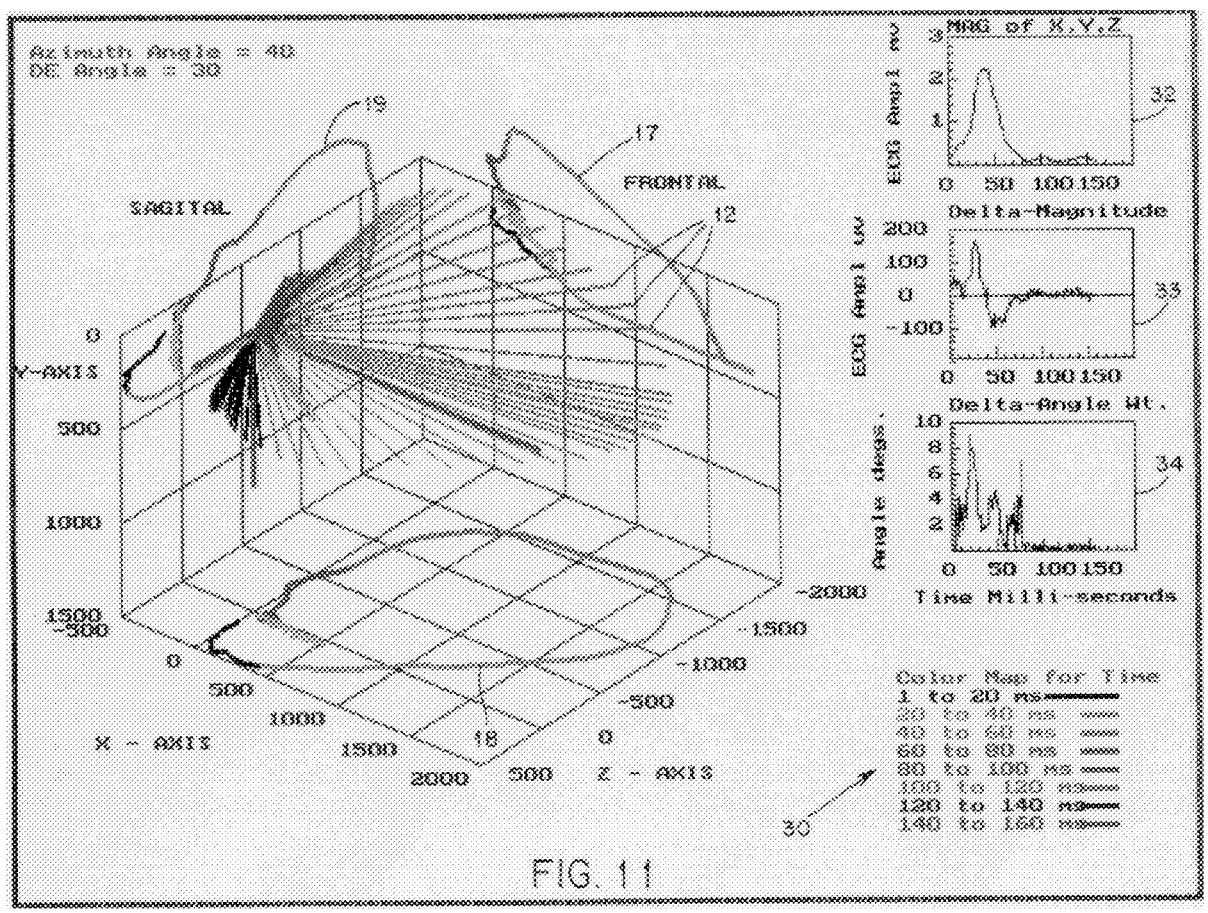
FIG. 11 is a 3-D cardiographic vector display of event No. 9 of FIG. 7.
Figure 12:
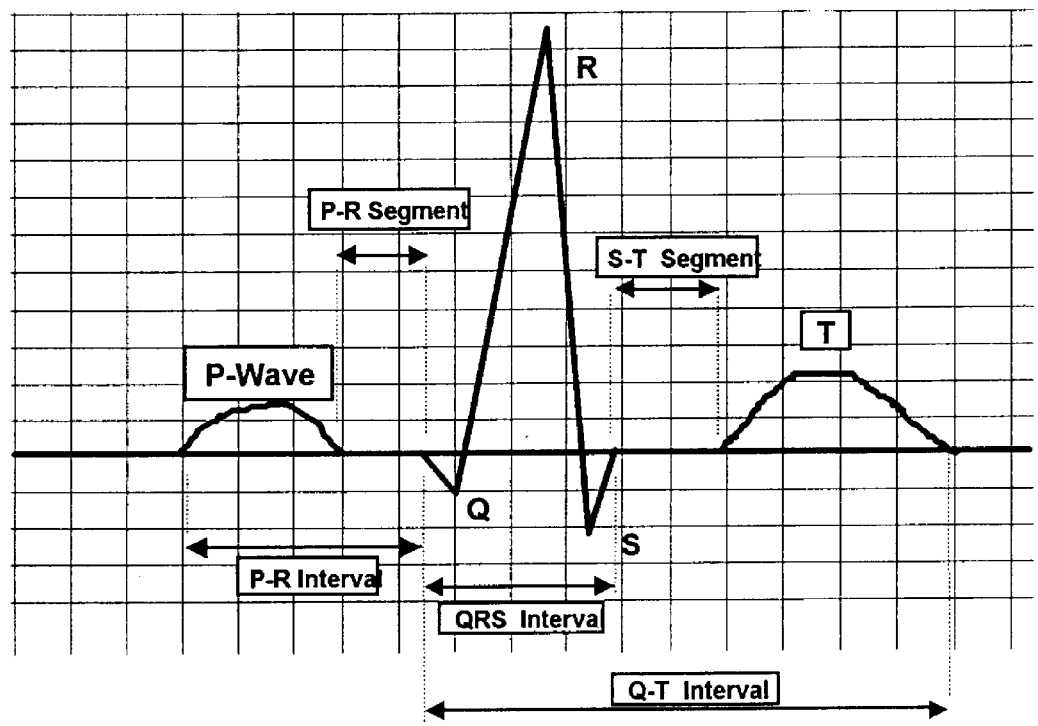
FIG. 12 is a graphical representation of an electrocardiogram showing the deplorization and repolarization of the heart muscle.

FIG. 7 shows the detection of the heart QRS complex by an algorithm 46 that looks at one of the X, Y or Z axis signals that has the most rapid increase in signal level at the outset. The signal being used is shown in the upper trace, in this case the X channel 50, and the detector output 52 in shown in the lower trace. A ten second interval is shown. The next four figures, i.e., FIGS. 8–11, show the 3-D vectorgram 10 for events 6 through 9 depicted on FIG. 7. As can be appreciated from the present disclosure, there are small variations from one 3-D display 10 to the next which it is believed may prove to be useful in diagnosing certain disease conditions.

From the present description, those skilled in the art will appreciate that various other modifications may be made without departing from the scope of the present invention. For example, while the display shows single line representations of the vectors at various time intervals over the QRS signal, in some instances it may be desirable to fill in the spaces between some or all of the vectors with a solid color, e.g., modeling, which may, in some circumstances, help in the visualization process. It is also possible to employ the technique of rendering a 3-D surface so as to show the effects of shading as the result of lighting from various sources.

Although the various figures illustrate the QRS complex portion of the ECG signal as a function time, it may be desirable to isolate or highlight other portions of the ECG signal. In fact, it is believed that other portions of the signal, if displayed in the same or similar manner as the QRS signal, may show other heart conditions which were difficult to easily recognized.

As noted in the illustrated cases, the QRS complex was sampled at 1 ms intervals In some cases it may be desirable to sample the QRS or another portion of the signal at longer or shorter intervals, e.g., about 0.5 ms. In addition, the T-wave 42 interval is combined on the same display and sampled at 5 ms intervals since this signal does not change as rapidly. However, in some cases it may be desirable to sample the T-wave 42 at shorter or longer intervals as well.

The data that has been used for examples are signal averaged over many heart cycles and have reduced the noise due to random effects to a minimum over a 200 second ECG data set. These data sets have also removed ECG beats that are ectopic or otherwise dissimilar from the normal beats. The original ECG analogue data was filtered by a bandpass filter from 0.05 hertz to 250 hertz. The 250 hertz filter is a bessel design which preserves the original waveform with minimum distortion.

What is claimed is:

1. A cardiographic display for displaying an electrocardiograph heart signal having a magnitude and location in vector format within a single three-dimensional coordinate system sampled at incremental time intervals, comprising:
    a point of origin;
    a three-dimensional coordinate system comprising an x-axis, a y-axis and a z-axis extending from said point of origin;
    a frontal plane defined by the area between said x-axis and said y-axis;
    a sagittal plane defined by the area between said z-axis and said y-axis;
    a transverse plane defined by the area between said x-axis and said z-axis; and
    means for displaying the magnitude and location of said signal within said coordinate system at incremental time intervals using a plurality of vectors, said vectors emanating from said origin.

2. A cardiographic display according to claim 1 wherein each said vector has a terminal point and said cardiographic display further comprises means for simultaneously projecting the terminal point of a plurality of said vectors in at least one plane.

3. A cardiographic display according to claim 2 wherein said projecting means projects the terminal point of a plurality of said vectors in each said plane.

4. A cardiographic display according to claim 3 further comprising means for distinguishing said vectors at different time intervals.

5. A cardiographic display according to claim 4 wherein said distinguishing means comprises means for changing the color of said vectors over said different time intervals.

6. A cardiographic display according to claim 2 further comprising means for displaying a T-wave and means for projecting a terminal point of said T-wave in at least one plane.

7. A cardiographic display according to claim 6 further comprising means for displaying a T-vector and means for projecting a terminal point of said T-vector in at least one plane.

8. A cardiographic dieplay according to claim 2 further comprising means for displaying a QRS-vector and means for projecting a terminal point of said QRS-vector in at least one plane.

9. A cardiographic display according to claim 2 further comprising means for displaying a P-wave and means for projecting a terminal point of said P-wave in at least one plane.

10. A cardiographic display according to claim 2 further comprising means for displaying an angle between a QRS vector and a T-vector.

11. A cardiographic display according to claim 1 further comprising means for displaying a change in magnitude between said plurality of said vectors.

12. A cardiographic display according to claim 1 further comprising means for displaying a change in angle between said plurality of sai(i vectors.

13. A cardiographic display according to claim 1 further comprising means for displaying a magnitude of said plurality of vectors.

14. A cardiographic display according to claim 1 further comprising means for displaying an off-set from the beginning of an ST segment using an ST vector, said displaying means for displaying said off-set emanating from said origin.

15. A cardiographic display according to claim 1 wherein said means for displaying further comprises means or displaying at least one Lead simultaneously with said cardiographic display.

16. A cardiographic display according to claim 1 wherein said means for displaying further comprises means for rotating said cardiographic display and said coordinate system.

17. A cardiographic display according to claim 1 wherein said means for displaying further comprises means for magnifying a particular area of said cardiographic display.

18. A cardiographic display according to claim 1 further comprising means for selectively changing said incremental time intervals.

19. A cardiographic display according to claim 1 wherein the change in magnitude and location between at least two successive vectors is distinguished.

20. A cardiographic display for displaying an electrocardiograph heart signal having a magnitude and location in vector format within a single three-dimensional coordinate system sampled at incremental time intervals, comprising:
   a point of origin;
   a three-dimensional coordinate system comprising an x-axis, a y-axis and a z-axis extending from said point of origin;
   a frontal plane defined by the area between said x-axis and said y-axis;
   a sagittal plane defined by the area between said z-axis and said y-axis;
   a transverse plane defined by the area between said x-axis and said z-axis; and
   means for simultaneously displaying the magnitude and location of said signal within said coordinate system at incremental time intervals using a plurality of vectors, the change in magnitude between said plurality of said vectors and at least one Lead.

21. A cardiographic display according to claim 20 wherein said means for displaying further comprises means for displaying the changes in magnitude the magnitude of said plurality of vectors.

22. A cardiographic display for displaying an electrocardiograph heart signal in vector format within a single three-dimensional coordinate system sampled at incremental time intervals, comprising:
   a point of origin;
   a three-dimensional coordinate system comprising an x-axis, a y-axis and a z-axis extending from said point of origin;
   a frontal plane defined by the area between said x-axis and said y-axis;
   a sagittal plane defined by the area between said z-axis and said y-axis;
   a transverse plane defined by the area between said x-axis and said z-axis; and
   means for displaying the magnitude and location of said signal within said coordinate system at incremental time intervals using a plurality of vectors;
   means for displaying a P-wave; and
   means for projecting a terminal point of said P-wave in at least one plane.

23. A method for displaying an electrocardiograph heart signal having a magnitude and location in vector format within a single three-dimensional coordinate system sampled at incremental time intervals, comprising the steps of:
   displaying a point of origin;
   displaying a three-dimensional coordinate system comprising an x-axis, a y-axis and a z-axis extending from said point of origin which defines a frontal plane located between said x-axis and said y-axis, a sagittal plane located between said z-axis and said y-axis, and a transverse plane located between said x-axis and said z-axis; and
   displaying the magnitude and location of said signal within said coordinate system at incremental time intervals using a plurality of vectors.

* * * * *